United States Patent [19]

Palluet

[11] 4,263,513
[45] Apr. 21, 1981

[54] APPARATUS FOR PANORAMIC RADIOGRAPHY

[75] Inventor: Jean-Noel Palluet, Paris, France

[73] Assignee: Compagnie Generale de Radiologie, Paris, France

[21] Appl. No.: 24,182

[22] PCT Filed: Feb. 28, 1979

[86] PCT No.: PCT/FR78/00011
§ 371 Date: Mar. 26, 1979
§ 102(e) Date: Feb. 28, 1979

[87] PCT Pub. No.: WO79/00065
PCT Pub. Date: Feb. 22, 1979

[51] Int. Cl.³ ............................................. G03B 41/16
[52] U.S. Cl. ................................................ 250/439 P
[58] Field of Search .................................... 250/439 P

[56] References Cited

U.S. PATENT DOCUMENTS 3,636,349  1/1972  Faude .............................. 250/439 P Primary Examiner—Craig E. Church
Attorney, Agent, or Firm—Roland Plottel

[57] ABSTRACT

An apparatus for panoramic radiography of a curved surface such as a dental arch, with an oscillating arm (17) holding an X-ray source (18) at one end and a film-carrier (20) at the other. The arm (17) is mounted free on an axle (16), called the third axle, which a mechanism causes to move along an elliptical trajectory adapted to the jaw of the patient. The arm is also driven in rotation around the third axle by a mechanism (stub 11, slot 24) connected to the primary axle (4) of the mechanism producing the ellipse so that it is always orthogonal to the ellipse. Film (19) is so driven as to prevent deformations of the panoramic projection. The ellipse is described at a variable speed to compensate for the absorption due to the cervical column.

7 Claims, 8 Drawing Figures

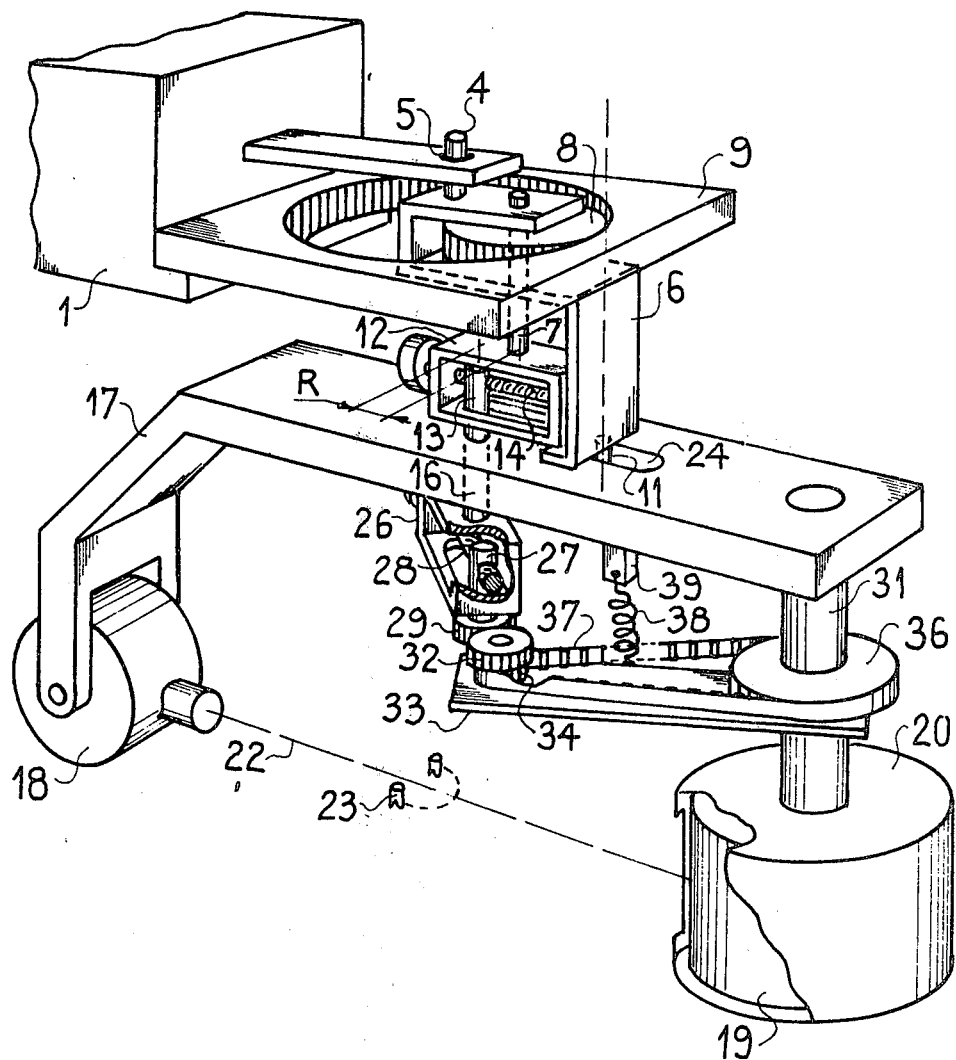
FIG_1

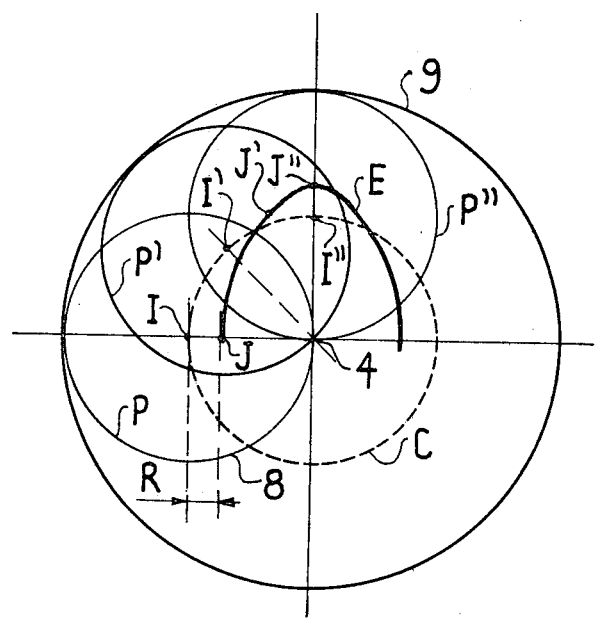
FIG_2
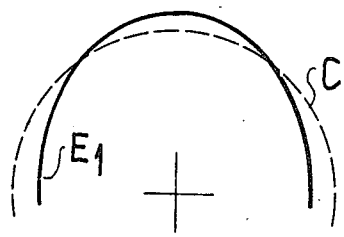
FIG_4·a
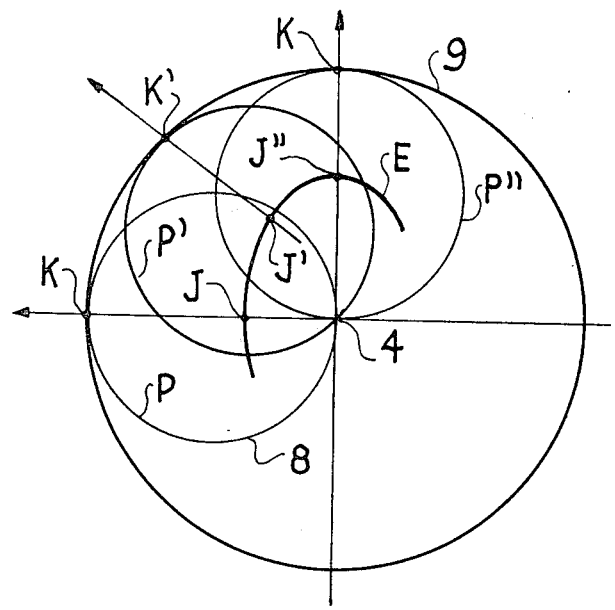
FIG_3
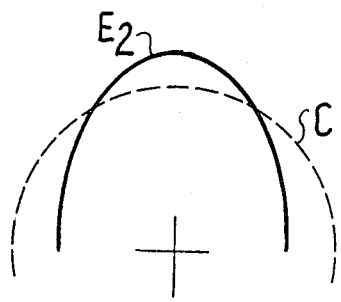
FIG_4·b
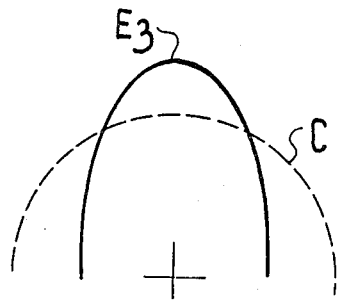
FIG_4·c

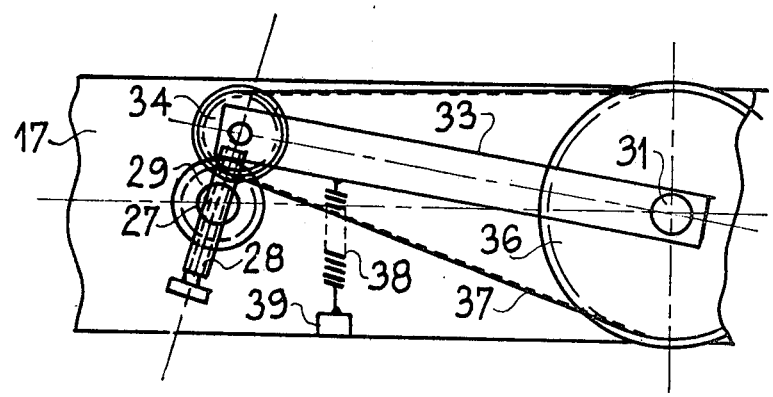
FIG_5
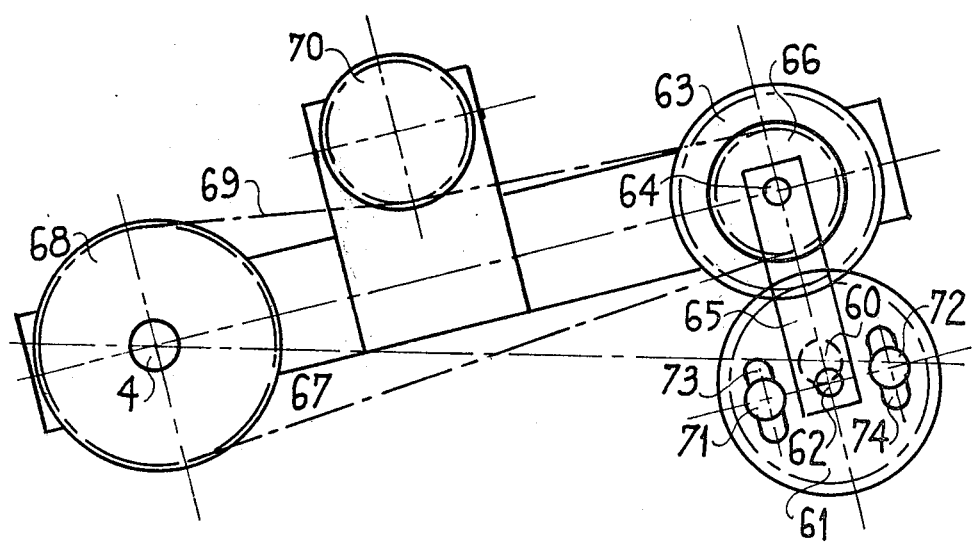
FIG_6

APPARATUS FOR PANORAMIC RADIOGRAPHY

The invention covers an apparatus for panoramic radiography of a curved surface and of the dental arch in particular.

Such an apparatus consists mainly of a stand holding an oscillating arm from which are suspended the X-ray source and the film holder. The arm moves round the surface to be X-rayed describing a curve as near as possible to that of the surface whose image is required. In practice, in order to be suitably adapted to the elliptical shape of the dental arch, this curve should be an ellipse whose lengthening should be adjusted as nearly as possible to the form of the jaw to be X-rayed. If this were not the case, a deformed projection of the various areas X-rayed would be obtained on the X-ray film.

U.S. Pat. No. 3,636,349 delivered on Jan. 18, 1972 describes a panoramic radiography apparatus in which an arm holding the X-ray source at one end and the film container at the other moves round the head of the patient with two combined motions. For this purpose the arm is attached to a vertical axis which moves along a curve similar to the shape of the jaw on the one hand and rotates around itself on the other. THe collimated beam of X-rays thus strikes the various points of the fixed jaw as the direction of the beam is variable with respect to a fixed mark.

This movement is obtained, in a first version in which the curve described by the axle holding the moving arm is part of a circle, by fixing this axle to the centre of a toothed satellite pinion, which is engaged inside a fixed toothed crown whose diameter is about twice that of the satellite pinion.

A motor reduction gear drives in rotation around itself a part which itself drives the axle mentioned in a circular movement round the centre of the toothed crown. When the axle moves thus over a half circle, it drives the satellite pinion which rolls without sliding in the crown and turns roughly a full turn since the ratio of the diameters is about 2:1.

The axle then drives the source-carrying and film-carrying arm which moves round the dental arch and rotates round itself. It should be noted that the direction of movement of the axle over the portion of circle it describes and the direction of rotation of this axle about itself are opposite. It should also be noted that, as the arm rotates about itself by a quantity which is imposed on it by the rotation of the satellite pinion in the crown, the arm, which is fixed to it, and hence the X-ray beam are far from being always orthogonal to the jaw in the zone covered by the rays.

In a second version of this apparatus, the source-carrying and film-carrying arm is mounted on the axle, which is operated as previously described, by means of a part whose eccentricity is adjustable. When the axle moves along its circle rotating about itself as described above, the axle holding the arm describes a portion of ellipse whose curvature may be adjusted by the aforementioned eccentricity. The movement of the arm may thus follow better the shape of the jaw. However, the non-orthogonality of the X-ray beam with respect to the jaw remains. The projection of the various zones X-rayed on the radiography film is made differently and the panoramic image of the jaw on the film is deformed.

One purpose of the invention is to produce an apparatus enabling a panoramic photograph of the jaw to be obtained without any deformation or fuzziness. This is possible if the tube-carrying and film-carrying arm is always perpendicular to the dental arch.

For this purpose, in an apparatus in accordance with the invention, which has a source-carrying and film-carrying arm mounted on an axle, which a mechanism with a satellite pinion engaged in a toothed wheel causes to move along an elliptical curve, the arm is mounted free on the axle which drives it and can rotate round this axle which forms an axis of rotation for it. Thus this axle drives the oscillating arm in its elliptical movement without imposing a fixed direction on it. The direction of the arm is given by an auxiliary controlling device which controls it in rotation around its axis of rotation in such a way that it is always normal to the tangent to the ellipse described by the said axis of rotation.

As one of the causes of deformation of the projection is thus eliminated by this combination of the two driving and controlling devices of the arm which they force to remain always orthogonal to the ellipse described by its axis of rotation, other sources of deformation of the panoramic photograph are eliminated or reduced by the apparatus of the invention. The other sources of possible deformation of the panoramic image projected are related to the displacement of the film on which the X-ray image is projected as it is produced. In the direction of the height of the teeth, there will be a constant deformation on the image projected which is equal to the enlargement due to the projection. This enlargement is a function of the ratio of the distances focal point—film and focal point—dental arch. To prevent deformations, it is therefore advisable that an equivalent enlargement of the arch developed in the direction of its length be obtained, the enlargement in this direction depending in particular on the movement of the film in its support.

For this it is necessary that the length of the dental arch on the film be a function of the length of the ellipse described by the axle driving the arm to within the enlargement factor and that the speed of displacement of the film behind the slot in the film holder be proportional to the speed of movement of this axle along its elliptical trajectory. However, the film holder is fixed on the arm which, on top of the elliptical movement given to it by the axle which drives it, has a rotational movement around this axle. The apparatus in the invention includes a film driving mechanism which enables the film running speed to be proportional to the speed of movement of the axle along its ellipse.

The apparatus in the invention also enables an X-ray photo of good quality to be obtained thanks to a mechanism fitted between the motor reduction gear and the satellite pinion device which enables the axle to be moved and drive the arm at a variable speed along the ellipse it describes to compensate for the variations in absorption of the X-rays in particular when the beam has to cross the spine.

Other purposes, characteristics and results of the invention will appear from the following description which is given as a non-limiting example and is illustrated by the figures attached which show:

in FIG. 1, a schematic view in perspective of a way of making a panoramic X-ray apparatus in accordance with the invention, in FIGS. 2 and 3, curves enabling the mode of operation of such an apparatus to be understood, in FIGS. 4a, 4b and 4c, curves showing different forms of the ellipse obtained, in FIG. 5, a part plan view of the film running device, in FIG. 6, a plan view of a possible way of making the mechanism driving the satellite pinion device.

In FIG. 1 at 1 can be seen the body of the stand resting on the ground, this part not being shown. A motor reduction gear unit, which is not shown, drives in rotation a primary axle 4, which turns in a bearing 5 that is attached to body 1. Primary axle 4 is fixed to an S-shaped part 6. In part 6 a secondary axle 7 turns and on this axle is fixed a toothed satellite pinion 8 which engages inside a toothed crown 9 fixed to body 1. The diameter of toothed satellite pinion 8 is half that of toothed crown 9. S-shaped part 6 has a stub 11 which will be discussed later. The end of secondary axle 7 has at its lower end a support block or slide-holder 12. This slide-holder 12 has, on its lower side, a slot in which a slide formed by a nut 13, which can be manoeuvred by an excentring screw 14, can move. Nut 13 is parallel to the primary and secondary axles, which are parallel to one another, but screw 14 is perpendicular to them. It enables the distance R to be varied between secondary axle 7 and nut 13 which is extended, at its lower end, by a third axle 16, which is parallel to the primary and secondary ones.

It is possible, in a simplified version of the apparatus in the invention, to replace slide-holder 12 and its adjustable slide by a fixed link between axles 7 and 16. In this case, R is constant.

The oscillating arm 17 is mounted free on third axle 16. Hence, it can rotate freely around this third axle which forms an axis of rotation for it. Arm 17 has a elongated slot 24, which is roughly parallel to the X-ray beam 22. Stub 11, which was mentioned above, is engaged in slot 24.

Oscillating arm 17 has at one of its ends an X-ray source 18 and at its other end a film-holder box 20 (in the shape of a drum for example).

The X-ray source emits a beam 22 in the direction of a slot arranged in box 20. This beam passes through the dental arch 23 of a patient installed for this purpose by a known device, which is not shown.

Film 19 is driven in box 20 as to pass in front of a slot in the box which lets the X-rays through. The device driving film 19 will be described in detail by means of FIG. 5. It may be noted that this device drives the drum holding film 19 but not box 20. This box is fixed directly on arm 17 itself by a device which is not shown. It does not rotate with the drum as the slot must always be opposite the X-ray source.

The operation of the apparatus in the invention will now be described by means of FIGS. 2, 3 and 4 in particular.

When primary axle 4 is driven by the motor reduction gear, S-shaped part 6 rotates with it and drives secondary axle 7 whose axis describes a circle around primary axle 4. In FIG. 2 are shown, by their pitch-circle diameters, toothed crown 9 and toothed satellite pinion 8, whose diameter is half that of the other, as seen from above. The centre of toothed crown 9 corresponds to the axis of primary axle 4. The centre I of toothed pinion 8 corresponds to the axis of secondary axle 7. Hence point I describes a circle C around point 4. When secondary axle 7 rotates thus around 4, toothed satellite pinion 8 engages the inside of toothed wheel 9, moving for example from a first position P to a second P' and then to a third P", etc. Its centre I (the axis of the secondary axle) moves respectively from I to I' and then to I" along circle C.

While toothed pinion 8 is thus moving (without sliding) along crown 9, a point on its circumference (corresponding to its pitch-circle diameter) describes a straight line and some point J, which is between centre I and this circumference, describes an ellipse. If the point J considered is at a distance R from I, the trajectory J' J" etc. that it covers is an ellipse E whose major axis is D+2R and whose minor axis is D−2R (D being the pitch-circle diameter of pinion 8).

Point J is the axis of third axle 16 which thus describes an ellipse whose curvature is determined by the adjustment of the distance R=IJ, i.e. the adjustment of excentring screw 14. Adjustment of this screw enables a circle to be obtained for R=0 (circle C) and ellipses which are more and more elongated as R increases. FIG. 4 shows what such ellipses look like, $E_1$, $E_2$ and $E_3$ compared with circle C for R=0.

It is thus easy to adapt the shape of the ellipse to the shape of the jaw to be X-rayed. In the simplified version previously mentioned in which R is not adjustable, a value of R is chosen which corresponds to a standard jaw.

The operation of the mechanism which has just been described causes the movement of third axle 16 along an ellipse (whose plane is perpendicular to the said axle). An additional mechanism, which is combined with this, thanks to the fact that arm 17 is mounted free on the third axle, will enable this arm to be normal to the tangent to the ellipse for all positions of axle 16. This mechanism contains slot 24, which is parallel to the axis of the arm, and stub 11, which is fixed to S-shaped part 6. Stub 11 is placed on part 6 directly below the tangent point of crown 9 and pinion 8. FIG. 3 makes it possible to understand how this stub and slot, when combined with the mechanism driving the arm along an ellipse, carry out this function.

Stub 11, directly below the tangent point of crown 9 and pinion 8, (in the plane view of FIG. 3) is in the various positions K, K' and K" when third axle 16 describes ellipse E (the axis of this axle being projected on J, J' and J"). The straight lines KJ, K'J' and K"J" are always normal to the tangents to ellipse E at J, J' and J" respectively.

Thus stub 11 which, when it slides in slot 24 of arm 17, is always on the longitudinal axis of this arm, keeps this axis confounded with straight lines KJ, K'J', K"J", etc. and keeps the arm orthogonal to the tangent to the ellipse. X-ray beam 22 is thus always perpendicular to the part of the jaw through which it is passing.

FIG. 5 shows in plan a view from below of the film running mechanism to a larger scale than that in FIG. 1.

This mechanism includes (FIG. 1) a support block or slide-holder 26, which is fixed to the lower end of third axle 16. A slide, which passes through a slot on the lower face of this slide-holder and is formed by a nut 27, can be moved in its slide-holder by shifting an excentring screw 28. Screw 28 is in a plane perpendicular to the axes of the aforementioned axles. Nut 27 is fixed to a toothed pinion 29 which then rotates with third axle 16 although eccentric with respect to it at a distance which is adjustable by excentring screw 28.

A lever 33, which can rotate around axle 31, which itself rotates in arm 17, has at its other end a couple formed by a toothed pinion 32 and notched wheel 34. Toothed pinion 32 mates with pinion 29 while a notched belt 37 connects notched parts 34 and 36. A spring 38 (FIG. 5) which is stretched between lever 33 and a part 39 hanging from arm 37 draws lever 33 towards the axis of the arm and enables toothed pinion 32 to be mated with pinion 29 no matter what the eccentricity of the axis of pinion 29 with respect to axle 16.

This film running device, as was said above, enables a constant enlargement of the photograph to be obtained independently of the curvature of the ellipse described. It makes this possible because it causes film 19 to run behind the slot in film-holder 20 at a speed proportional to the speed of third axle 16 along its elliptical trajectory.

As a result of the arrangement shown in FIG. 5 film-holder 19 is caused to rotate by pinion 29 through pinion and notched pulleys 34 and 36. This rotational movement is the sum of two movements, the rotational movement of pinion 29 driven by third axle 16 and a movement of the axis of pinion 29 with respect to third axis 16 of oscillation of arm 17. This second movement is a function of the eccentricity fixed by excentring screw 28. It is adapted to the curvature of the ellipse described by the axis of axle 16 by excentring pinion 29 by means of screw 28 by an amount proportional to the excentring R produced by screw 14. The proportionality between the eccentricities is a function of the ratios between the diameters of pulleys and pinions 29 to 36. The correct enlargement of the photographs is obtained by a suitable choice of the said ratios. Once these ratios have been fixed, a correspondence is determined for the eccentricity to be produced by screw 28 as a function of that adopted for screw 14 when the ellipse is adjusted on the dental arch. It should be noted that, if distance R is constant, when the third axis (18) is connected to the second axis (7) by a fixed part as already indicated, the excentring of pinion 29 with respect to axis 16 can also be constant and the fixing ensured by a non-adjustable part.

Thus, as has already been said, it is advisable that ellipse E be not described at a constant speed by third axle 16 which drives the arm so that the photograph is not underexposed in the zone of the incisors where the X-ray beam passes through the dense zone formed by the cervical column before striking the incisors and then the film.

A solution in certain apparatuses of preceding practice consists in correcting this fault by increasing the X-ray penetration, and hence the source voltage, when passing this region.

In the apparatus of the invention, this correction takes place automatically and then mechanically only.

It is interesting to note a property of the apparatus of the invention before coming to the correction mechanism properly speaking which prevents the bad effects of the cervical column.

By accepting, in the absence of this corrective mechanism, that primary axle 4, and hence toothed pinion 8, rotates at a constant speed, the apparatus already produces a precorrection. When pinion 8 rotates at constant speed in wheel 9, point J (FIG. 3) moves more slowly in the zone of high curvature of ellipse E. However, this precorrection, which is intrinsically related to the method for obtaining the movement of the arm in accordance with the invention, may prove insufficient to compensate for the effect of the cervical column especially as it is reduced by a counter-effect. If point J moves more slowly in the zone of high curvature, the normal (K'J', K"J", etc.) to the ellipse turns more quickly in this zone of high curvature. Hence there is a slower elliptical movement of the arm but a faster rotation of this same arm around its axis of rotation (third axle 16).

The correction device which enables an (adjustable) slowing of the movement speed along the ellipse to be obtained when the incisors are passed consists in modifying the rotational speed of primary axle 4 in a non-uniform fashion.

FIG. 6 shows, seen from above, a way of obtaining, with the apparatus of the invention, a photograph which is not underexposed in the zone of the incisors thanks to a variable speed of rotation of primary axle 4. This variable speed of axle 4 is obtained by adding, between axle 60 of the motor reduction gear and primary axle 4, a device formed as follows. A toothed pinion 61, whose geometrical axis 62 can be excentred in adjustable fashion with respect to axis 60 of the motor reduction gear, is mounted on axis 60 of the motor reduction gear. Pinion 61 engages a toothed pinion 63 of the same diameter as itself which turns freely around an axis 64. This axis 64 is connected to the geometrical axis 62 of pinion 61 by a connecting rod 65 whose length is equal to the pitch circle diameter of pinions 61 and 63. Thanks to this connecting rod, the engagement of the two pinions is always ensured. Also, it is mounted free on axis 62 and 64.

A chain pinion 66 is mounted coaxially with pinion 63 to which it is fixed. This chain pinion 66 rotates freely with respect to axis 64 like pinion 63.

Axis 64 is fixed on a second connecting rod 67 which can rotate around axle 4 which is the primary axle of the apparatus in the invention.

On axle 4 a chain pinion 68, the number of whose teeth is double that of pinion 63, is solidly fixed. Pinion 63 drives pinion 68 in rotation by means of a chain 69 held taut by a roller 70 mounted on rod 67.

The excentring of pinion 61 with respect to axis 60 of the motor reduction gear which drives the whole can be adjusted, for example, by means of screws 71 and 72 which are fixed to axle 60 of the motor reduction gear, these screws passing in slots 73 and 74 of pinion 61. The excentring depends on the position of these screws in the slots.

This device works as follows.

If there is no excentring, axis 60 and 62 are coaxial and the speeds of rotation of the various pinions are constant because the motor reduction gear rotates at constant speed. The connecting rods do not move and axle 4 rotates at a speed half that of axis 60 of the motor reduction gear.

If, on the other hand, axis 62 is excentred with respect to axis 60 of the motor reduction gear, a variation in the rotational speed of primary axle 4 is introduced. While pinion 61 rotates at constant speed, pinion 63 and pinion 66, which is fixed to it, rotate at variable speed with the maximum and minimum a half turn apart. Connecting rod 67 oscillates round axis 4 which forms the centre of the system.

As the reduction is $\frac{1}{2}$ between pinions 66 and 68, axle 4, which is driven by pinion 68, rotates at a variable speed but with two maxima and minima per rotation.

When the excentring between axes 60 and 62 is suitably chosen, a greater or lesser slowing down of the elliptical movement of source-carrying and film-carrying arm 17 can be programmed at the instant it passes to the right of the patient's incisors. The choice of this excentring can be made, for example, as a function of the homogeneity of the blackening of the panoramic photographs for the average patient.

It may also be noted that an interesting effect results from the combination of the two causes of speed variation in the movement of third axle 16 along its elliptical trajectory, the one being the variation in speed given to primary axle 4 by a suitable device such as that described, the other being the variation inherent in the mechanism of production of the ellipse (as described above). Because of this combination, the minimum and maximum arm speeds are not 90° apart but at an angle which is a function of the excentring of pinion 61. The following operation results: the arm starts in a low speed zone and accelerates; it again slows down in the incisor zone, reaccelerates and ends its movement at slow speed.

This operation has the advantage that it causes the arm to start up at slow speed with an unsynchronized motor, and hence at constant speed, which enables, the starting oscillations visible on photographs to be eliminated.

We claim:

1. In an apparatus for panoramic radiography containing, on a stand (1), a motor reduction gear device driving a primary axle (4) in rotation around itself, this axle (4) driving in its turn, in rotation around itself, a secondary axle (7) which is parallel to it and carries a toothed satellite pinion (8) which, when the secondary axle moves, engages inside a fixed toothed crown (9) at their tangent point, a third axle (16), parallel to the other two, being fixed to the secondary axle in such a way as to be at a predetermined distance R from said secondary axle, so that third axle (16) moves along an ellipse (E) when primary axle (4) is operated, the value of said distance R defining the shape of said ellipse, this third axle (16) sustaining an oscillating arm (17) having at one of its ends, an X-ray source (18) which emits a collimated X-ray beam (22) towards a film-holder (20) fixed to the other end of the arm, said film-holder (20) having a slot exposed to the X-ray beam and a device for displacing the film (19) behind said slot in said film-holder according to the arm (17) movements, the improvement consisting in that:

the diameter of said fixed toothed crown (9) is double that of said satellite pinion (8) so that, when said primary axle (4) makes a full turn around itself, said satellite pinion (8) makes two turns in said fixed crown (9);

said arm (17) is mounted free on said third axle (16) which thus drives said arm in its elliptical movement without determining its direction, said arm being rotatable about said third axle (16) which constitutes its rotation axis;

and the longitudinal direction of said arm (17), and consequently the direction of said X-ray beam, is controlled by an auxiliary controlling device having coupling means (11) linked to said primary axle (4) so that it rotates with it and penetrating in an elongated slot (24) of said arm (17), said slot (24) being parallel to the longitudinal axis of said arm and aligned with its rotation axis, and said coupling means (11) being aligned with a line parallel to said axles and passing through the tangent point of said toothed crown (9) and said satellite pinion (8); in such a way that, for each position of said third axle (16) along said ellipse (E), the longitudinal direction of said arm (17) is orthogonal to said ellipse.

2. An apparatus as in claim 1, wherein said primary axle (4) is coupled to the axle (60) of the motor reduction gear, which is rotating at constant speed, by a device which makes the speed of rotation of this primary axle variable with two maximums and minimums per turn of the primary axle, a speed minimum occuring when third axle (16) is at the peak of ellipse (E) which it describes.

3. An apparatus as in claim 2, wherein said device, which is fitted between axle (60) of the motor reduction gear and said primary axle (4) comprises: a third toothed pinion (61) driven by said axle (60) of the motor reduction gear from which it is adjustably excentred, a fourth toothed pinion (63) of the same diameter as the third which is held engaged with it by a first connecting rod (65), this fourth pinion (63) being itself mounted at one end of a second connecting rod (67), which may rotate, at its other end, round said primary axis (4), a couple of pinions (66,68), which reduce speed in the ratio of one to two and are coupled together by a chain (69), first pinion of this couple being coaxial with and fixed to said fourth toothed pinion (63) while second pinion (68) of this couple drives primary axle (4).

4. An apparatus according to claim 1, wherein said coupling means (11) of said auxiliary controlling device for arm (17) comprises a stub (11), which is fixed on a part (6) attached to said primary axle (4).

5. An apparatus as in claim 1 or 4, characterized by the fact that third axle (16) is fixed to second axle (7) by a support block (12) fixed to the secondary axle and having a nut (13), which can be moved perpendicularly to secondary axle (7), said nut (13) being positioned by an excentring screw (14) and holding the third axle, the adjustment of screw (14) enabling the curvature of ellipse (E) along which third axle (16) moves to be adjusted.

6. An apparatus as in claim 5, wherein the device for displacing the film (19) in its holder (20) has: an axis (31) rotating in said arm (17) and on which are said fixed film-holder (20) and a first notched pulley (36), a first toothed pinion (29) fixed to the third axle by a part such that this pinion is eccentric with respect to this axle, a second toothed pinion (32), which engages with the first (29) and is mounted on a lever (33) which rotates round axis (31) that holds the film-holder (19), a return spring (38) which ensures the permanent engagement of the said two pinions, a notched belt (37) connecting notched pulley (36) on the axis of the film-holder to a second notched pulley (34), which is fixed to second toothed pinion (32).

7. An apparatus according to claim 6, wherein said first toothed pinion (29) is fixed to said third axle (16) by a further support block (26) which is fixed to this third axle, said first toothed pinion (29) being itself fixed to a further nut (27) which is moved perpendicularly to the third axle by a further excentring screw (18) controlled according to the position of said excentring screw (14) which determines the curvature of ellipse (E) along which the third axle moves.

* * * * *